United States Patent [19]
Kuntz et al.

[11] Patent Number: 4,825,878
[45] Date of Patent: May 2, 1989

[54] LIGHT-WEIGHT DISPOSABLE PROTECTIVE FACE SHIELD

[76] Inventors: David H. Kuntz, 11810 Bel Terrace, Los Angeles, Calif. 90049; Louis F. Muller, 919 Main St., El Segundo, Calif. 90245

[21] Appl. No.: 138,070
[22] Filed: Dec. 28, 1987
[51] Int. Cl.⁴ .............................................. A61F 9/04
[52] U.S. Cl. .................................... 128/857; 128/858; 128/207.11; 2/9
[58] Field of Search .......... 128/132 R, 201.22, 201.23, 128/201.24, 206.12, 206.19, 206.21, 206.23, 206.24, 207.11, 207.17; 2/9, 12, 173, 206

[56] References Cited

U.S. PATENT DOCUMENTS

| | | | |
|---|---|---|---|
| 1,323,217 | 11/1919 | Darrow | 128/201.11 X |
| 2,294,593 | 9/1942 | Bailey | 128/132 R |
| 2,631,287 | 3/1953 | Malcolm, Jr. | 2/9 |
| 2,665,686 | 1/1954 | Wood et al. | 128/206.12 |
| 2,829,374 | 4/1958 | Malcolm, Jr. | 2/9 |
| 4,258,437 | 3/1981 | Sawatsky | 2/12 |
| 4,292,689 | 10/1981 | Townsend, Jr. | 2/12 |
| 4,293,958 | 10/1981 | Zauner | 2/12 |
| 4,386,277 | 5/1983 | Forshee | 2/9 X |
| 4,589,408 | 5/1986 | Singer | 128/132 R |
| 4,594,999 | 6/1986 | Nesbitt | 128/134 X |
| 4,619,254 | 10/1986 | Moretti et al. | 128/201.23 |
| 4,621,378 | 11/1986 | Hatchman | 2/12 X |
| 4,665,566 | 5/1987 | Garrow | 128/201.22 X |

Primary Examiner—Robert A. Hafer
Assistant Examiner—Kevin G. Rooney
Attorney, Agent, or Firm—Philip D. Junkins

[57] ABSTRACT

A light-weight, disposable face shield assembly for the protection of the eyes and face of wearers from accidental exposure to infectious, hazardous or undesirable substances. The shield includes a semi-flexible shield frame surrounding a semi-flexible, transparent face protection panel and a semi-flexible head support strip having an operative length less than the length of the upper horizontal frame portion and positioned adjacent the rear side thereof. The support strip is affixed at its ends to the shield assembly proximate the ends of the upper frame portion. Flexible face shield ties are affixed to the shield assembly proximate each end of the upper frame portion for tie joinder at the rear of the head of the wearer of the shield assembly, such shield ties upon oppositely pulling and tie joinder together behind the head of the shield wearer resulting in the forming up of the shield frame member with the face protection panel in arcuate spaced orientation from the head support strip about the face of the wearer in rigidly supported fashion by the head support strip.

12 Claims, 3 Drawing Sheets

LIGHT-WEIGHT DISPOSABLE PROTECTIVE FACE SHIELD

BACKGROUND OF THE INVENTION

The present invention relates to face shields for the protection of the eyes and face of wearers from accidental exposure to infectious, hazardous and undesirable substances. More particularly, the invention relates to anti-infection shields for the protection of health care workers and professionals and laboratory personnel from accidental exposure to infectious and/or hazardous fluids and particulate materials.

Health care workers have long recognized that caring for patients with certain infectious diseases poses risks of contracting such diseases. For example, many cases have been reported of accidental transmission of Hepatitis B from patients to persons involved in their care. More recently, the life threatening epidemic of Acquired Immunodeficiency Syndrome (AIDS) caused by the Human Immunodeficiency Virus (HIV) has aroused great concern. Although the bulk of cases of patient to health care worker cross infection have resulted from accidental needle-sticks, medical office, hospital, surgical, dental and laboratory personnel are now required to use extreme care in the handling of all patients and body fluids as potentially infected with HIV and other pathogens. Particular attention has been directed to the risk to surgeons and operating room personnel of infection through splashing or splattering of blood or other body fluids onto open wounds, into mouths or into the eyes of such personnel during the performance of surgical procedures.

In the United States, the Centers for Disease Control, Public Health Service of the U. S. Department of Health and Human Services, has issued a comprehensive series of recommendations for the prevention of HIV transmission in health care settings and such recommendations are applicable to the risks of exposure to all infected body fluids. These recommendations show an increasing concern for protection of the eyes (particularly conJunctiva) if aerosolization or splashing of blood or other fluids is likely to occur. Thus, according to the Centers for Disease Control, eye shields should be worn by medical personnel and laboratory workers to prevent blood and other body fluids from splattering into the eyes. An effective eye shield must protect the eyes no matter which direction the wearer faces. Ordinary eyeglasses are not sufficient protection.

It is an object of the present invention to provide a face shield for the protection of the eyes and face of wearers from accidental exposure to infectious, hazardous and undesirable substances.

It is another obJect of the invention to provide a face shield for the protection of health care workers and profession also and laboratory personnel from accidental exposure to body fluids from infected patients.

It is a further obJect of the invention to provide a low-cost, disposable face shield for health care workers and profession and laboratory personnel subject to accidental exposure to infectious body fluids.

Another object of the invention is to provide a light-weight, full-face shield for the protection of the eyes and face of health care and laboratory personnel from spattered blood and other body fluids containing infectious disease forms.

Yet another obJect of the invention is to provide a light-weight, protective face shield for a wide variety of worker-wearers exposed to infectious, hazardous and undesirable substances.

Still another object of the invention is to provide a light-weight, disposable protective face shield which is readily formed up from a flat packaged form and may be worn over ordinary eyeglasses.

Other objects and advantages of the invention will become apparent from the following summary and detailed description of preferred embodiments of the invention taken in conjunct ion with the accompanying drawing figures.

SUMMARY OF THE INVENTION

The present invention relates to light-weight, disposable face shields for the protection of the eyes and face of wearers from accidental exposure to infectious, hazardous and undesirable substances. It is of particular interest in the protection of health care workers and professionals and laboratory personnel from accidental exposure to body fluids from infected patients. The shield includes; a semi-flexible, initially flat frame structure supporting an elongated, generally-rectangular, transparent eye/face protection panel; and a semi-flexible head support strip (in one or two strip parts) with head strip ties each affixed to the shield frame and interacting with ends of the head strip so that when the ties are pulled about the wearer's head, and tied together at the rear thereof, the shield frame (with its eye/face protection panel) forms up in arcuate outwardly spaced fashion about the wearer's head and the transparent panel provides full face protection while allowing total peripheral vision by the wearer.

The frame structure of the face shield preferably is formed of semi-flexible sheet plastic material or coated paper board and includes an elongated upper horizontal frame portion with depending side or leg portions. In another form the frame may include a lower horizontal frame portion interconnected to the lower ends of the depending side frame portions. The frame structure is affixed to the front or rear side of the semi-flexible eye/face protection panel formed of relatively thin optically clear polyester sheet material or other appropriate clear plastic sheet material. The clear eye/face protection panel may be coated with an anti-glare substance (compatible with the panel material) where the face shield is to be worn under high lighting conditions. The frame structure of the face shield may be comprised of one or more substantially like sheets of plastic or paper board with one of the frame sheets affixed to the front side and the other of the sheets (if utilized) affixed to the rear side of the eye/face protection panel.

In its unformed orientation (for flat packaging and/or storage), the head support strip lies adjacent to the rear side of the frame structure along the upper horizontal frame portion. The head strip is somewhat shorter (operative length) than the horizontal frame portion of the frame structure. In a first embodiment of the face shield structure, each end of the head support strip includes tie ports and head strip ties are affixed proximate each outboard end of the upper horizontal frame portion are back-threaded through the tie ports of the head support strip, and extend outwardly of the shield for pulling to form up the shield in forwardly projecting spaced fashion from the head strip (and the wearer's head) and to tie the head strip and supported shield to the wearer's head. Through the head strip and tie mechanisms of the shield structure the applied shield is rigidly formed in arcuate configuration and supported on the wearer's head with great stability. In a second embodiment of the face shield structure, the head support strip actually is comprised of two strip parts in end-to-end orientation. The outboard end of each strip part is affixed to the upper horizontal frame portion proximate end thereof. The inboard ends of the strip parts are provided with means for overlapped connection to one-another to form a head support strip (when the shield is readied for use) having an operative length somewhat shorter than the length of the upper horizontal frame portion between the points of attachment of the outboard ends of the strip parts to such frame portion thereby causing the shield structure to form up in arcuate fashion with respect to the connected strip parts. Flexible face shield ties are affixed to each end of the upper horizontal frame portion proximate the points of attachment of the strip parts for pulling the head support strip and attached face shield structure around the forehead of the wearer to further form up the shield to its final forwardly projecting (arcuate) spaced position with respect to the wearer's head and to tie the head strip and supported shield to the wearer's head.

BRIEF DESCRIPTION OF THE DRAWING FIGURES

DETAILED DESCRIPTION OF THE PREFERRED EMBODIMENTS

Figure 1:
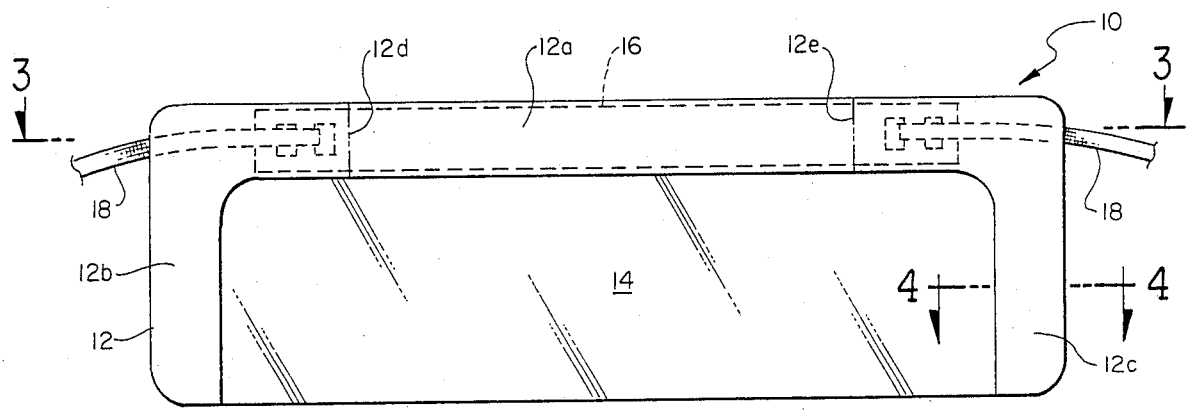
FIG. 1 is a front view of the eye/face shield of the invention with the shield in its unformed orientation for flat pack aging or storage.
Figure 2:
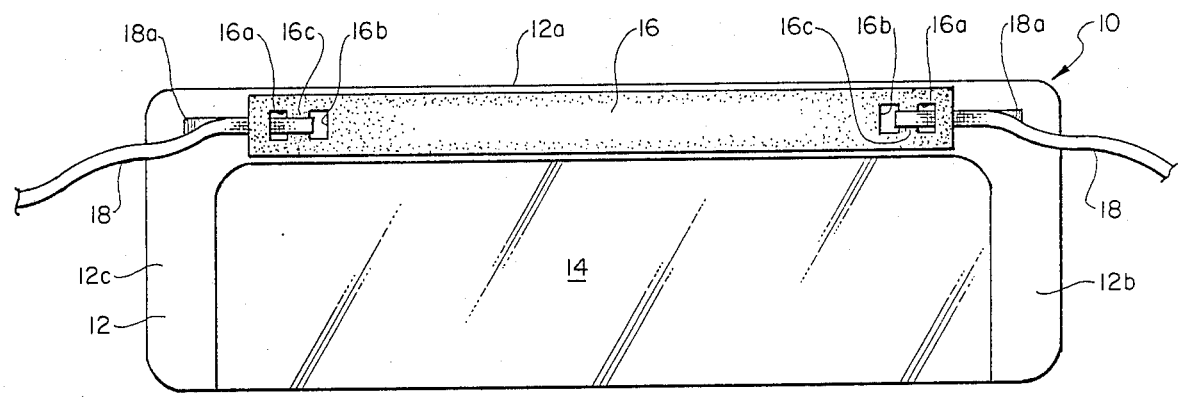
FIG. 2 is a rear view of the eye/faceshield of FIG. 1 with the shield in its unformed orientation.
Figure 5:
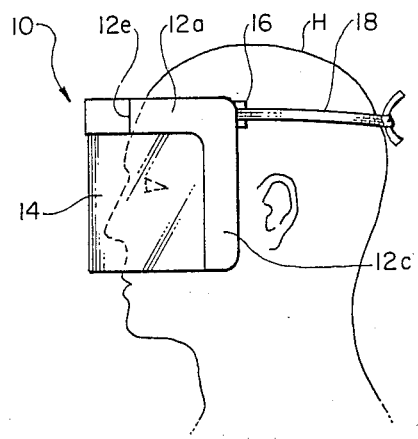
FIG. 5 is a side view of the eye/face shield of the invention in operative protective position tied on the head of a wearer of the shield.
Figure 6:
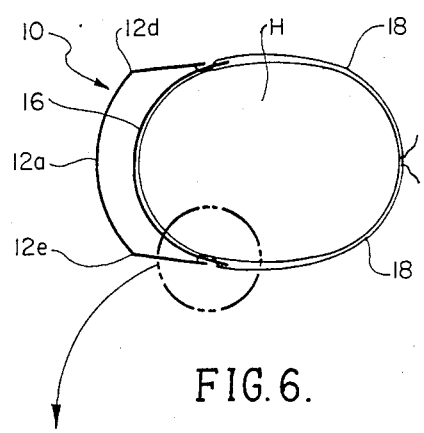
FIG. 6 is a top view of the eye/face shield of the invention in operative protective position tied on the wearer's head.

Referring initially to FIGS. 1 and 2 there is illustrated front and rear views, respectively, of a preferred form of the eye/face shield 10 of the invention with the shield in its unformed or preformed orientation for flat packaging or storage. The shield includes as its principal elements: a semi-flexible, flat frame structure 12 supporting an elongated, generally-rectangular, transparent eye/face protection panel 14; and a semiflexible head support strip 16 with head strip ties 18 each affixed to the shield frame 12 at strip ends 18a and interacting with the ends of the head strip so that when the ties 18 are pulled about the wearer's head (and tied together at the rear thereof) the shield frame 12 (with its transparent eye/face protection panel 14) forms up in arouate spaced fashion about the wearer's head as shown in FIGS. 5 and 6. As shown in FIGS. 5 and 6 the transparent panel 14 provides eye and face protection while allowing total peripheral vision by the wearer.

Figure 4A:
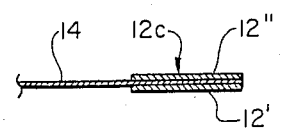
FIG. 4a is a partial sectional view of one form of the shield frame structure taken through a leg portion of the shield on line 4—4 of FIG. 1.
Figure 4B:
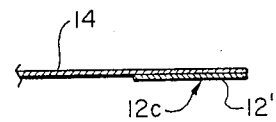
FIG. 4b is a partial sectional view of another form of the frame structure taken through the leg portion of the shield on line 4—4 of FIG. 1.

The frame structure 12 of the eye/face shield 10 preferably is formed of semi-flexible sheet plastic material or coated paper board and includes an elongated upper horizontal frame portion 12a with depending side or leg portions 12b and 12c. The frame structure 12, as shown in the partial sectional view of frame leg portion 12c in FIG. 4a, is comprised of two frame structure sheets 12' and 12" affixed to the front side and rear side, respectively, of the semi-flexible, transparent eye/face protection panel 14 formed of relatively thin optically clear plastic sheet material such as polyester plastic sheet material. Alterntively, the frame structure 12, as shown in the partial sectional view of frame leg portion 12c in FIG. 4b, is comprised of a sing frame structure sheet 12' affixed to the front side (only) of the transparent panel sheet 14. As a further alternative frame structure, a single frame structure sheet may be affixed to the rear side (only) of the panel sheet 14.

Figure 3:
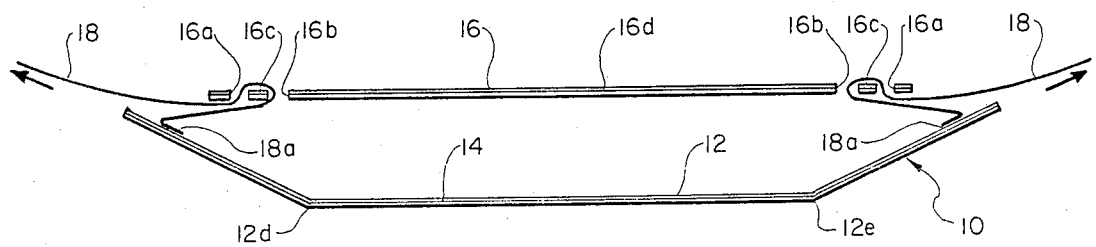
FIG. 3 is a top sectional view of the eye/face shield of FIG. 1 taken on line 3—3 of FIG. 1, but with the shield in its partially formed orientation by the longitudinal pulling of the head strip ties.

In the shield's unformed or preformed orientation (for flat packaging and/or storage), the head support strip 16 lies adjacent to the rear side of the frame structure 12 along the upper horizontal frame portion 12a as shown in FIG. 2. It is to be noted that the head support strip 16 is somewhat shorter in length than the horizontal frame portion 12a and the ends of the head support strip 16 each include tie ports 16a and 16b. The tie ports at each end of head strip 16 are separated by a tie strut 16c. The head strip ties 18 may be made of any suitable strong flexible synthetic or natural fiber strip material. The ties 18, at their ends 18a, are each affixed to the upper horizontal portion 12a of the frame structure 12 at a point on such frame portion intermediate the end of the head support strip and the end of such frame portion as shown in FIGS. 1 and 3. Affixation of the tie ends 18a to the frame structure portion 12a may be accomplished by any appropriate means including adhesive affixation, heat welding of the parts if made of plastic materials, rivets, etc. As shown in FIGS. 2 and 3, each of the head strip ties 18 extends inwardly between the frame structure portion 12a and head support strip 16 to inner tie port 16b and is then back threaded through tie port 16b, over tie strut 16c and through the outer tie port 16a. Thereafter the ties each extend longitudinally and oppositely for an appropriate length for pulling wardly to form up the shield frame structure 12 in forwardly projecting spaced fashion from the head strip 16 and for tying the head strip 16 (and the frame structure 12 that it supports) to the wearer's head. FIG. 3, particularly, shows (through a top sectional view) the initial stage of forming up the eye/face shield 10 when first pulling (oppositely) the strip ties 18.

Figure 6A:
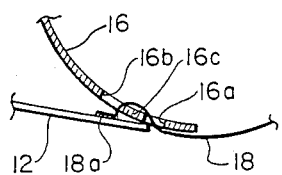
FIG. 6a is an enlarged partial top view of the eye/face shield of FIG. 6 showing the shield frame to head strip connection system as maintained by a head tie.

It will be noted from FIG. 1 that score lines 12d and 12e are provided across upper horizontal frame structure portion 12a and from FIGS. 3 and 6 that such score lines result (upon the opposite pulling of strip ties 18) in a partial folding of the frame structure 12 at such score (fold) lines. Upon full pulling of strip ties 18 to the point whereat the ends of the heat strip 16 extend slightly beyond the outer edges of the upper frame structure portion 12a (and no further movement of the head strip 16 with respect to shield frame structure 12 is possible as shown in FIG. 6a) the eye/face shield 10 is fully formed and may be tied to the wearer's head H, as shown in FIGS. 5 and 6. The tension of ties 18 causes firm abutment of the outer edges of the upper frame structure portion 12a to the end portions of head strip 16 whereby rigidity and stability is established between the shield frame structure 12 and the head strip 16 so that the head strip (when tied to the wearer's head) firmly supports the eye/face shield 10 in proper spaced and full protective alignment with the wearer's head H.

As shown in FIG. 3, the head strip 16 may be provided with an absorptive liner or facing layer 16d of cloth, soft foam plastic material or absorptive paper for absorbing forehead moisture as my be generated by the wearer during use of the shield. It should be understood that the leg portions 12b and 12c of the frame structure 12 may be of greater or lesser length to accommodate transparent eye/face protective panels 14 of different downwardly-extending widths.

Figure 7:
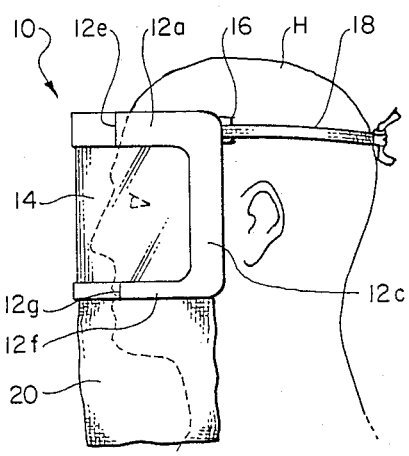
FIG. 7 is a side view of an alternative form of the protective eye/face shield of the invention on the wearer's head.

In FIG. 7 there is illustrated an alternative form of the protective eye/face shield of the invention. In such figure the protective eye/face shield 10 (shown in place on the wearer's head H) is provided with a semi-flexible frame structure 12 with a lower horizontal frame portion 12f (with score or fold line 12g) and such lower frame portion has affixed thereto a lower downwardly hanging curtain 20 of flexible, fluid resistant material for providing added protection to the wearer of the shield 10 from the splattering of body fluids that may be virus infected, i.e., protection to the neck area of the shield wearer.

Figure 8:
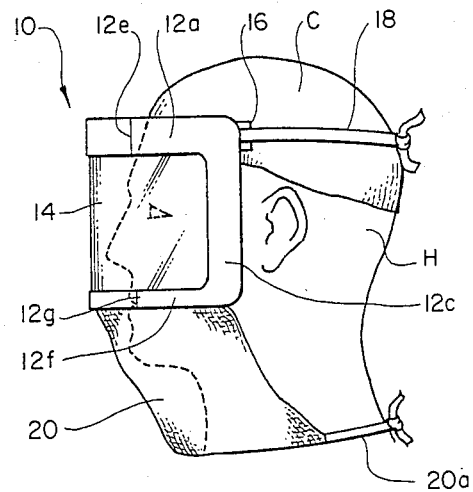
FIG. 8 is a side view of still another form of the protective eye/face shield of the invention on the wearer's head.

In FIG. 8 there is illustrated a further alternative form of the protective eye/face shield of the invention. In such figure the protective shield 10 (shown in place on the wearer's head H) is provided with a semi-flexible frame structure 12 comprised of upper frame portion 12a, side frame portion 12c and lower frame portion 12f and such lower frame portion has affixed thereto a downwardly hanging curtain 20 of flexible, fluid resistant material for providing added protection to the neck area of the wearer of the shield 10. As shown in FIG. 8 the curtain 20 is pulled rearwardly to the wearer's neck by ties 20a so that the curtain 20 acts as, and refaces in effectiveness, a typical surgical mask. The curtain-type surgical mask of disposable with the face shield assembly 10. The face shield assembly 10 may also be provided with adhesive means, Velcro type fasteners or other type fastener means along the inner surface of the head support strip (not shown in FIG. 8) for attachment of the face shield assembly to the lower front edge of a surgical cap C that may be worn by the wearer of the face shield.

Figure 9:
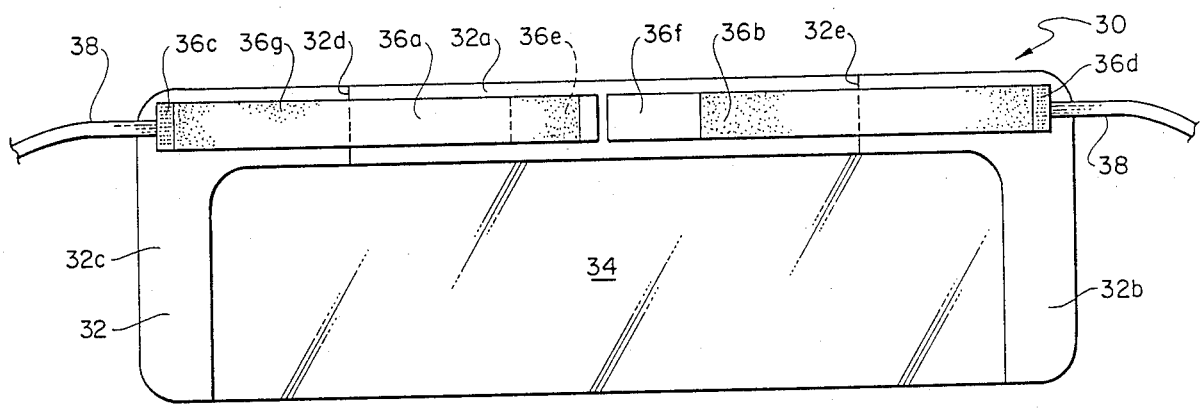
FIG. 9 is a rear view of yet another eye/face shield embodiment in accordance with the invention in its unformed orientation.
Figure 10:
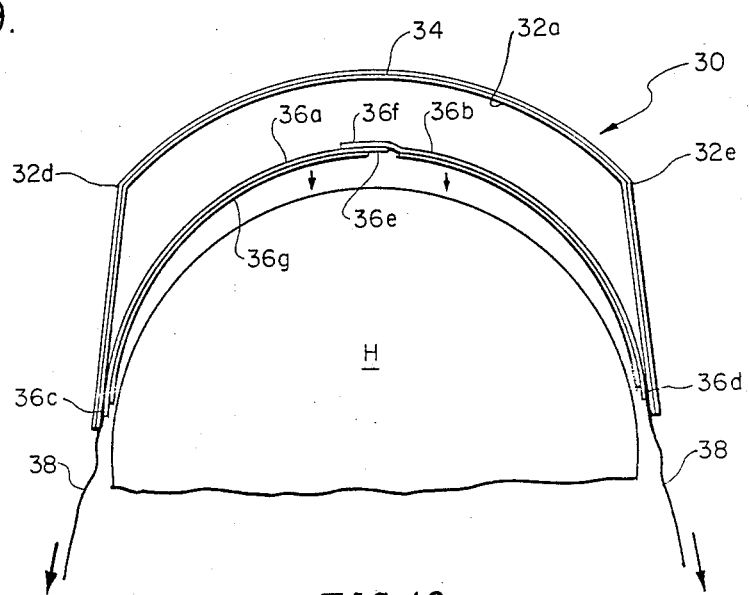
FIG. 10 is a top view of the eye/face shield of FIG. 9 in its nearly formed orientation by the longitudinal pulling of the head strip ties in position proximate the wearer's head.

In FIG. 9 there is illustrated the rear view of a further embodiment of the eye/face shield of the invention with the shield 30 in its unformed or preformed orientation for flat packaging or storage. The shield 30 includes as its principal elements: a semi-flexible, flat frame structure 32 supporting an elongated, strip parts 36a and 36b to such frame portion. When the flexible shield ties 38 are pulled about the wearer's head H, as shown in FIG. 10, and are tied together at the rear of the wearer's head, the shield frame 32 (with its transparent eye/face protection panel 34) forms up fully in arcuate spaced fashion about the wearer's head. As shown in FIG. 10, the face shield assembly is approaching its seated about the head H of the wearer. When fully seated and tied to the wearer's head, the transparent panel provides eye and face protection while allowing total peripheral vision by the wearer, even if the wearer is also wearing eyeglasses.

The frame structure 32 of the eye/face shield 30 of FIGS. 9 and 10 preferably is formed of semi-flexible sheet plastic material or coated paper board and includes, in addition to its elongated upper horizontal frame portion 32a, depending side or leg portions 32b and 32c. As in the case of the frame structure 2 of FIGS. 1 and 3, the upper horizontal frame portion 32a is provided with score lines 32d and 32e so that there is a partial folding of frame portion 32a at such score (fold) lines when the eye/face shield 30 is formed up for protective use. The frame structure may be comprised of two sheets affixed to the front side and rear side of the semi-flexible, transparent eye/face protection panel 34 or the frame structure may consist of a single sheet affixed to either the front or rear side of the eye/face panel.

The fact that the head strip parts 36a and 36b are assembled together at their respective ends 36e and 36f provides the wearer with a measure of adjustability as to the arcuate size of the head strip (see overlapped structure of the strip parts 36a and 36b at their respective end areas 36e and 36f as shown in FIG. 10). It should also be noted that the head strip parts 36a and 36b may be provided with an absorptive liner or facing layer 36g of cloth, soft foam plastic material or absorptive paper for absorbing forehead moisture as may be generated by the wearer during use of the shield.

In the specification and drawing figures there has been set forth preferred embodiments of a light-weight, disposable, anti-infection face shield for the protection of health care workers and professional and laboratory personnel from accidental exposure to body fluids from virus infected individuals, in accordance with the invention. Although specific terms have been employed in describing the invention, they are used in a generic and descriptive sense only and not for purposes of limitation, the scope of the invention being defined in the following claims.

What is claimed is:

1. A light-weight, disposable face shield assembly for the protection of the eyes and face of a wearer from accidental exposure to infectious, hazardous or undesirable substances, said face shield assembly in its substantially flat pre-use form including:
    (a) an elongated, semi-flexible shield frame member to which there is affixed an elongated, semi-flexible, transparent face protection panel;
    (b) an elongated, semi-flexible head support strip for said shield frame member in alignment therewith and having an operative length that is less than the length of said frame member;
    (c) means for attaching the ends of said shield frame member to the ends of said head support strip;
    (d) means for forming up said shield frame member and said affixed face protection panel in supported, arcuate spaced face protection orientation from said head support strip as a three-dimensional face shield assembly and maintained in position about the forehead of a wearer protects the eyes and face of the wearer.

2. A light-weight, disposable face shield assembly as claimed in claim 1 wherein said head support strip has two aligned tie ports proximate each end thereof and said means for attaching the ends of said shield frame member to the ends of said head support strip, said means for forming up said shield frame member and said affixed face protection panel in supported, arcuate spaced frame protection orientation, and the means for maintaining said support strip in position about the forehead of a wearer comprise two flexible face shield assembly ties each affixed at one end to said shield frame member proximate an end thereof and threaded inwardly between said shield frame member and said head support strip to the innermost of said tie ports, through said innermost tie port, outwardly to said outermost tie port, through said outermost tie port and outwardly of said face shield assembly whereby upon pulling said face shield assembly ties oppositely from one another the ends of said face shield frame member are drawn to the ends of said head support strip with outward forming up of aid frame member and said affixed face protection panel in supported, arcuate orientation from said head support strip and upon tying joinder of the other ends of said face shield assembly ties at the rear of a wearer's head said face shield assembly is maintained in protective position about the face of the wearer.

3. A light-weight, disposable face shield assembly as claimed in claim 1 wherein in said shield frame member includes an upper horizontal frame portion and downwardly depending side portions affixed to and framing said transparent face protection panel.

4. A light-weight, disposable face shield assembly as claimed in claim 1 wherein said shield frame member includes an upper horizontal frame portion and said frame portion includes vertical score lines each equally spaced from an end of said upper frame portion for assisting in the partial folding of said upper frame portion upon the pulling of said face shield ties and tying joinder of said face shield ties.

5. A light-weight, disposable face shield assembly as claimed in claim 1 wherein said shield frame member is formed of front and rear sheets of semi-flexible material affixed to and sandwiching said transparent face protection panel at its peripheral edge.

6. A light-weight, disposable face shield assembly as claimed in claim 1 wherein said shield frame member is formed of a front sheet of semi-flexible material affixed to said transparent face protection panel at its peripheral edge.

7. A light-weight, disposable face shield assembly as claimed in claim 1 wherein said shield frame member is is formed of a rear sheet of semi-flexible material affixed to said transparent face protection panel at its peripheral edge.

8. A light-weight, disposable face shield assembly as claimed in claim 1 wherein said shield frame member includes an upper horizontal frame portion, downwardly depending side portions and a lower horizontal frame portion joined at its ends to the lower ends of said downwardly depending side portions of said shield frame member.

9. A light-weight, disposable face shield assembly as claimed in claim 1 wherein the elongated, semi-flexible head support strip is divided proximate its midpoint into two end-to-end strip parts, said strip parts each extending inwardly from their respective means for attaching the ends of said shield frame member to the ends of said head support strip, and said strip parts having means at their respective inward end for connection to one-another whereby upon such connection the operative length of the upper horizontal said shield frame member of said shield assembly.

10. A light-weight, disposable face shield assembly as claimed in claim 9 wherein the means for connection of the strip parts of said head support strip includes connection means selected from the group consisting of mating Velcro fasteners, mating adhesive surfaces and mating snap fasteners.

11. A light-weight, disposable anti-infection face shield assembly for the protection of the eyes and face of health care workers and professionals and laboratory personnel from accidental exposure to infectious, hazardous or undesirable fluids and particulate substances comprising:

(a) an elongated, semi-flexible shield frame member formed of an upper horizontal frame portion with downwardly depending said portions;

(b) an elongated, semi-flexible, transparent face protection panel affixed to and carried by said shield frame member;

(c) an elongated, semi-flexible head support strip for said shield frame member in alignment therewith and having an operative horizontal length that is less than the length of said upper frame portion and positioned adjacent the rear side thereof, said head support strip having two aligned tie ports proximate each end thereof; and (d) two flexible head support strip ties each affixed at one end to said upper frame portion proximate and end thereof, each of said ties threaded inwardly between said support strip and said upper frame portion to the innermost of said tie ports, through said innermost tie portal, outwardly to the outermost of said tie ports, through said outermost tie port and outwardly of said face shield assembly whereby upon pulling said head support ties oppositely from one-another the ends of said shield frame member are drawn to the ends of said head support strip with outward forming up of said shield frame member and said affixed transparent face protection panel in supported, arcuate orientation from said head support strip and upon tying joinder of the other ends of said head support strip ties at the rear of a wearer's head said face shield assembly is maintained in protective position about the face of the wearer.

12. A light-weight, disposable anti-infection face shield assembly as claimed in claim 11 wherein the upper horizontal frame portion of said shield frame member includes vertical score lines each equally spaced from an end of said frame portion for partial folding of said frame portion upon tie pulling and tie joinder of said head support strip ties.

* * * * *